United States Patent [19]
Aranyi

[11] Patent Number: 5,116,349
[45] Date of Patent: May 26, 1992

[54] SURGICAL FASTENER APPARATUS

[75] Inventor: Ernie Aranyi, Easton, Conn.

[73] Assignee: United States Surgical Corporation, Norwalk, Conn.

[21] Appl. No.: 528,125

[22] Filed: May 23, 1990

[51] Int. Cl.⁵ .......................................... A61B 17/00
[52] U.S. Cl. ..................................... 606/142; 606/139
[58] Field of Search ............... 606/139, 140, 141, 142, 606/143

[56] References Cited

U.S. PATENT DOCUMENTS

| | | | |
|---|---|---|---|
| 3,780,416 | 12/1973 | Rider | 604/143 |
| 4,354,628 | 10/1982 | Green . | |
| 4,606,345 | 8/1986 | Dorband et al. . | |
| 4,665,916 | 5/1987 | Green | 604/143 |
| 4,728,020 | 3/1988 | Green et al. . | |
| 4,767,044 | 8/1988 | Green . | |
| 4,819,853 | 4/1989 | Green . | |
| 4,881,545 | 11/1989 | Isaacs et al. . | |

Primary Examiner—Randall L. Green
Assistant Examiner—R. Clarke
Attorney, Agent, or Firm—Thomas R. Bremer; Peter G. Dilworth; Rocco S. Barrese

[57] ABSTRACT

An apparatus for substantially simultaneously applying a plurality of two-part absorbable surgical fasteners to body tissue which includes biasing means to pivot the fastener holder into a final open position to release the body tissue. The biasing means is operable only after the fasteners have been applied.

24 Claims, 14 Drawing Sheets

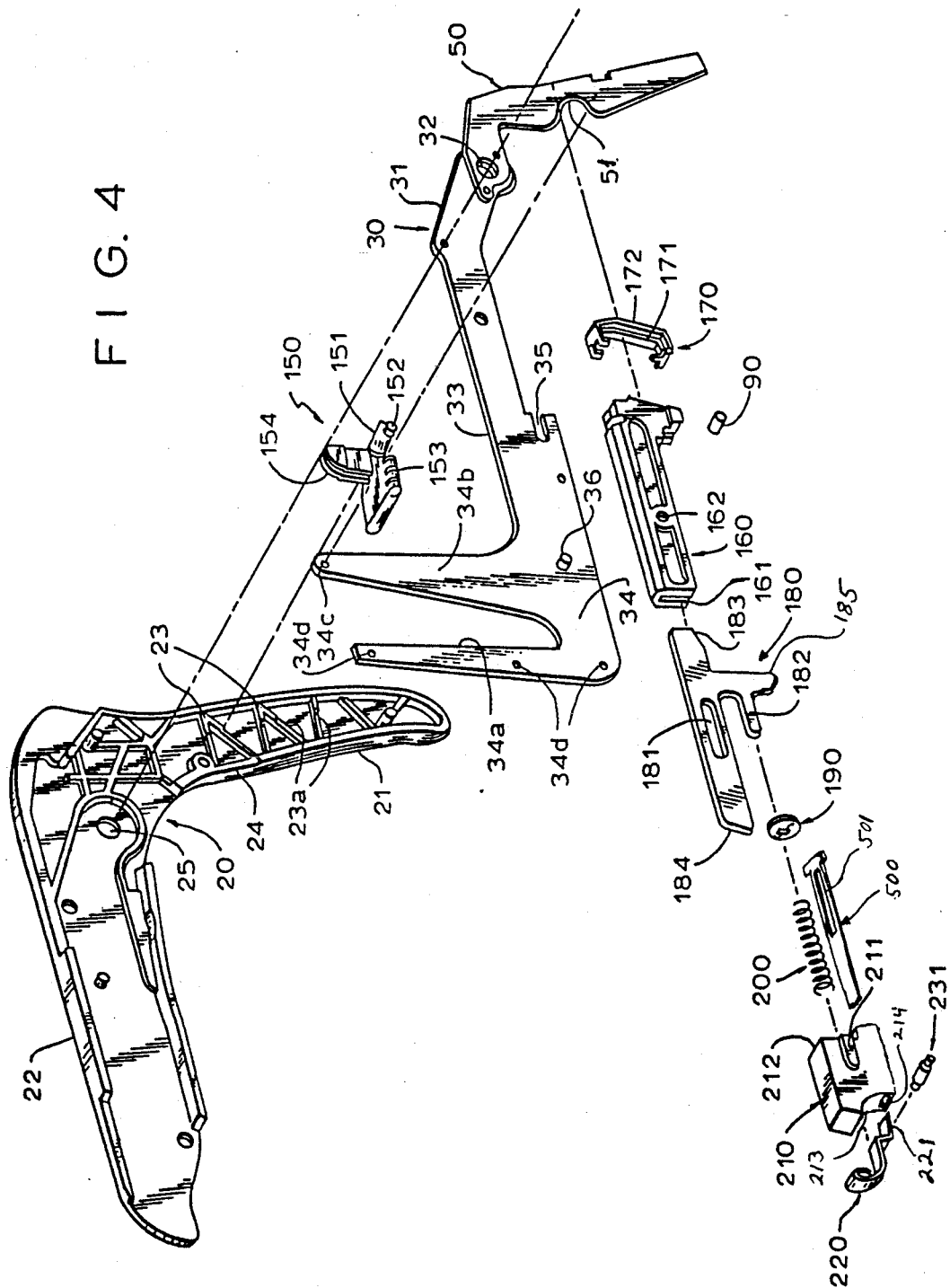

F I G. 7
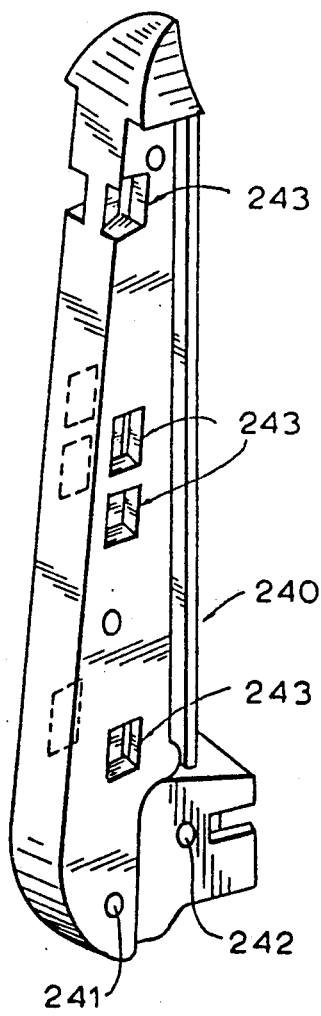
F I G. 8
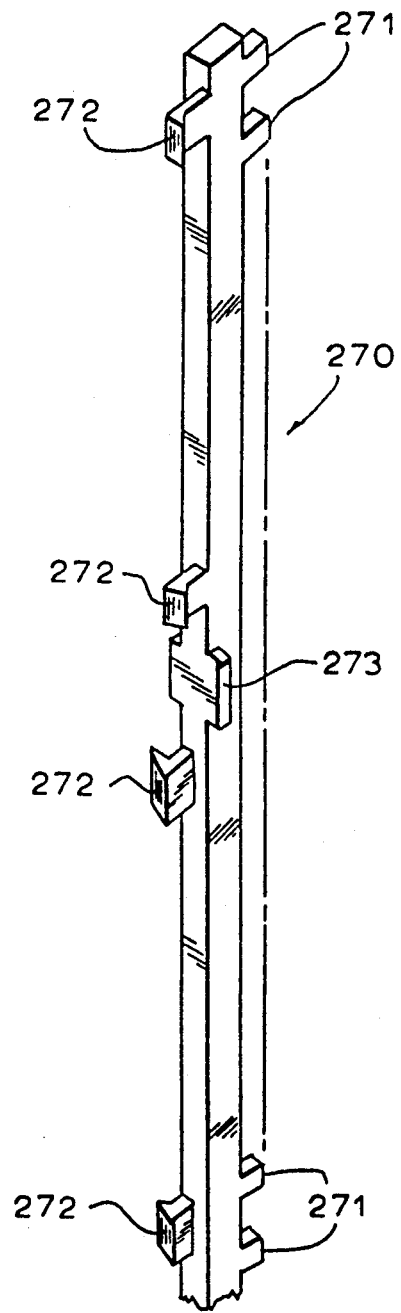

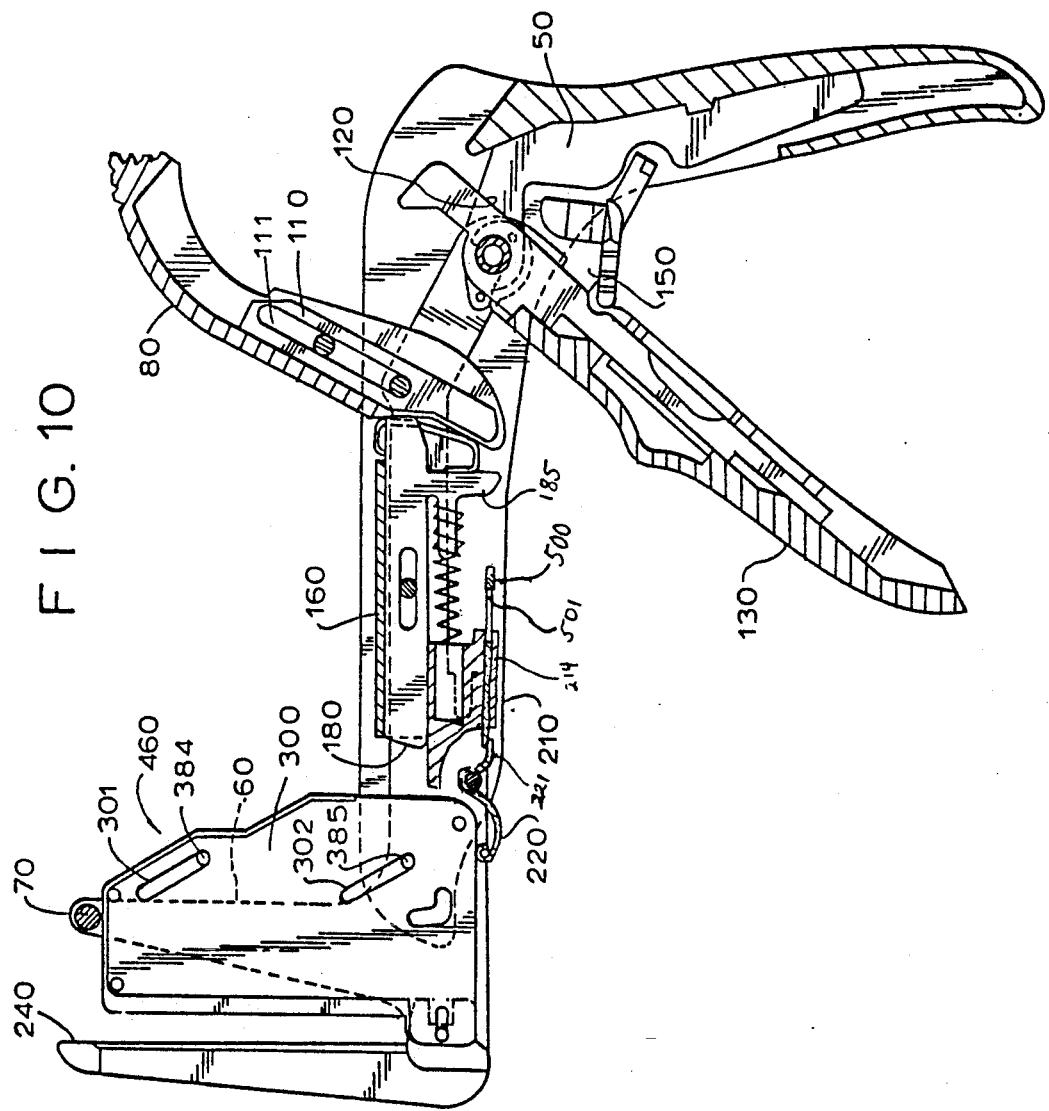

FIG. 14
FIG. 15
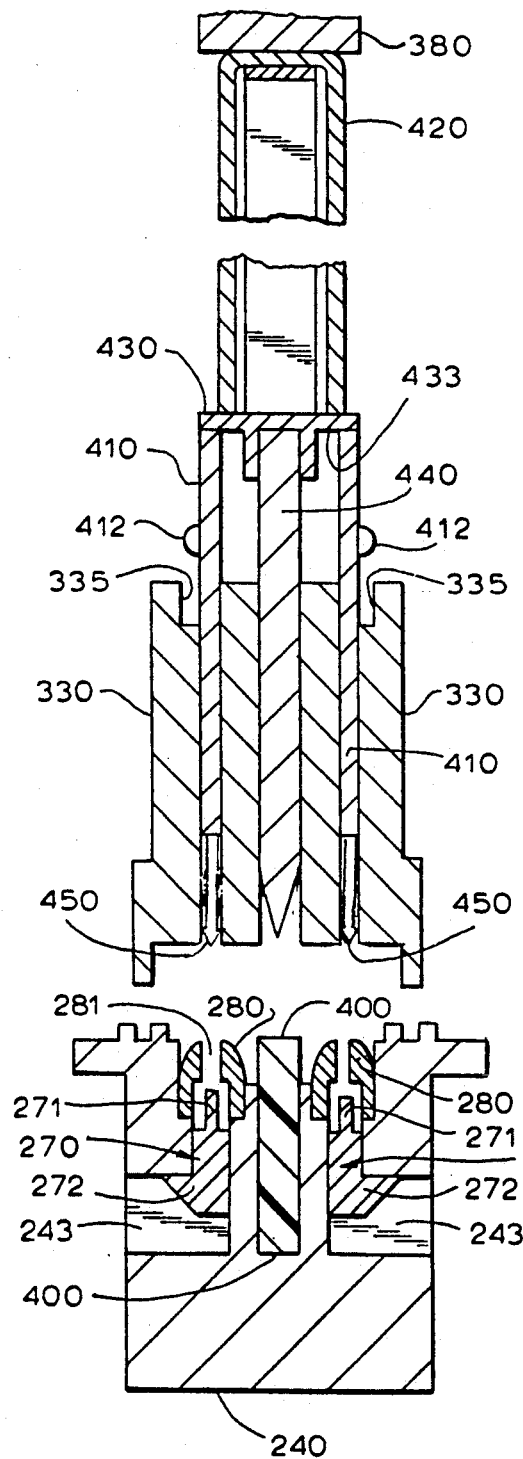
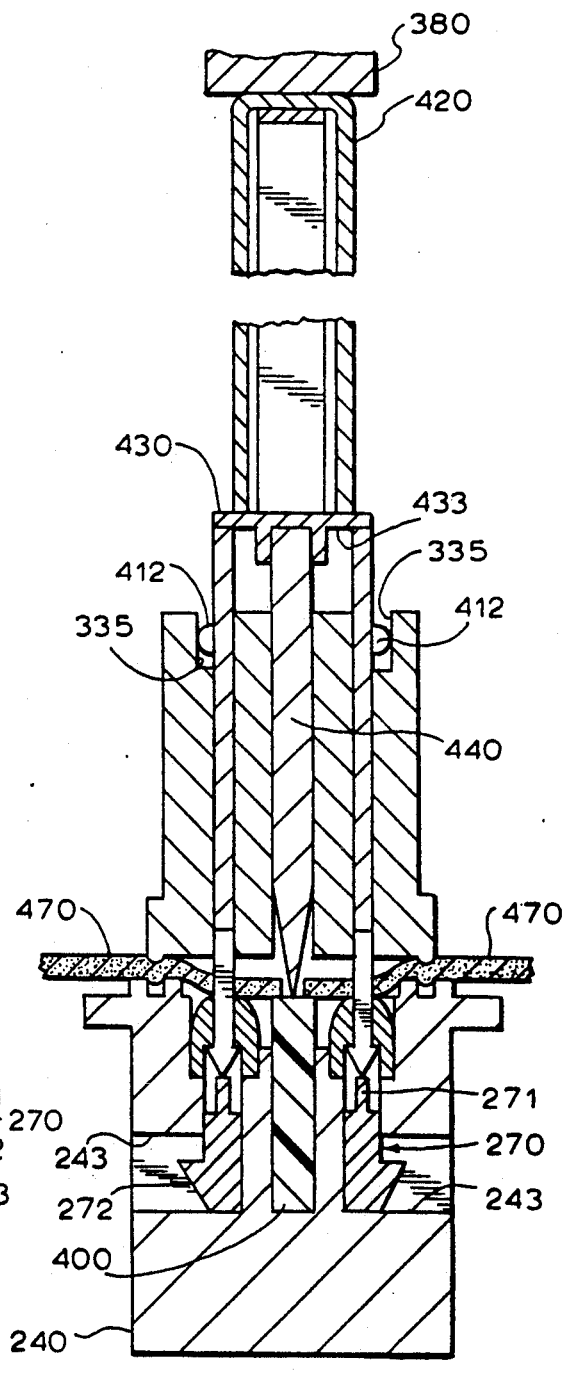

5,116,349

SURGICAL FASTENER APPARATUS

CROSS REFERENCE TO RELATED APPLICATIONS

This application is related by subject matter to commonly assigned copending application Ser. No. 07/458,182 filed Mar. 5, 1990.

BACKGROUND OF THE INVENTION

1. Field of the Invention

This invention relates to an apparatus for applying a plurality of surgical fasteners to body tissue and more particularly to an apparatus for simultaneously applying a plurality of two part bioabsorbable surgical fasteners.

2. Description of the Prior Art

Surgical fastener applicator apparatus in which surgical fasteners are simultaneously applied to body tissue are known. Typically, these devices include a fastener holder positioned on one side of the tissue to be fastened and an anvil parallel to the fastener holder positioned on the other side of the tissue. Typically, means is provided for linearly translating the fastener holder and the anvil toward one another to clamp the tissue between them. Means is also provided for driving the fasteners from the fastener holder so that the ends of the fasteners pass through the tissue and form finished fasteners as they make contact with the anvil assembly, thereby producing an array of finished fasteners in the tissue.

Also in use are instruments for applying two part fasteners having a fastener portion and a retainer portion. The fastener portion generally has barbed prongs for penetrating body tissue and engaging corresponding openings in the retainer portion. Once engaged, the fastener and retainer are locked together. Such two-part fasteners are usually constructed from bioabsorbable material.

In common use are apparatus in which the fastener holder and anvil are removably mounted in or on an actuator for supporting and actuating the cartridge. The apparatus can be disposed of after a single use or it can be reused for another surgical fastening procedure after cleaning, sterilizing and reloading with a fresh cartridge. Also in use are fully disposable surgical instruments in which the cartridge and actuator are preassembled ready for use and disposed of after only a single use.

U.S. Pat. No. 4,665,916 (Green) describes a surgical fastener apparatus for applying rows of fasteners laterally through hollow body organs such as the thorax, trachea, stomach, uterus or intestines. The cartridge includes an alignment pin which achieves and maintains proper relative positioning of the fastener holder and anvil components thereof. When the fully assembled instrument is actuated, it is positioned in such a way that the body tissue to be fastened is clamped in place between the staple-ejecting surface of the fastener holder and the anvil assembly. The clamping pressure exerted against both sides of the tissue is sufficient to provide effective hemostasis along two linear sites which, upon "firing" of the instrument, receive substantially parallel rows of fasteners on either side of an incision formed by a tissue cutting knife which is also incorporated in the holder. The deployment of the knife is mechanically synchronized to immediately follow the insertion of the fasteners.

U.S. Pat. No. 4,819,853 (Green) discloses a surgical fastener applicator which includes tissue gripping elements provided along the sides of a knife slot to prevent body tissue from pulling away from the fasteners after the latter are positioned in place and the incision is made. Thereafter, clamping pressure is released.

U.S. Pat. No. 4,881,545 (Isaacs et al.) discloses a surgical fastener cartridge possessing an improved body cutting knife assembly. The knife element of the assembly is held in permanent locking engagement with a knife holder.

U.S. Pat. No. 4,767,044 (Green) discloses a fastener applying apparatus including means for preventing all of the fasteners from reaching peak formation force at the same time in order to reduce the maximum force required to operate the apparatus.

U.S. Pat. No. 4,728,020 (Green et al.) discloses an articulated surgical fastener applying apparatus having a linear drive mechanism which is offset from the centerline of movement of the surgical fasteners. The drive force is proximally directed, i.e. it is a pulling force transmitted by a tensioned cable mechanism rather than by a drive rod.

While the prior art instruments, such as those mentioned above, have been serving the needs of the medical community by providing surgeons with quick and simple means to make and/or seal incisions in body tissue, improvements are nevertheless desirable. For example, in performing operations on the uterus, it is important not to cause damage to fetal tissue. The chance of such damage occurring is greatly reduced by having a closely controlled gap spacing between the fastener cartridge and the anvil assembly. Narrow gap clearance is preferred initially to minimize the possibility of extraneous tissue entry into the gap while the apparatus is open. However, after the apparatus is fired and opened to release the body tissue, a wide gap clearance is preferred to facilitate easy removal of the body tissue from the gap.

SUMMARY OF THE INVENTION

An apparatus is provided herein for applying a plurality of surgical fasteners to body tissue or the like by gripping body tissue between fastener holding means and fastener closure means, applying the fasteners to the body tissue, and closing the fasteners. The apparatus includes means for pivotally biasing at least one of said fastener holding means and said fastener closure means toward a position which provides separation of the body tissue from said fastener holding means and fastener closure means, the pivotal biasing means being operable only after the fasteners have been closed.

In a preferred embodiment the fasteners are simultaneously applied. The apparatus generally comprises a body, fastener closure means at one end portion of the body, and a fastener holder mounted relative to the fastener closure means. The fastener closure means, such as an anvil, and the fastener holder are biased toward an initial spaced position for receiving and contacting body tissue positioned between them. The apparatus includes releasable means for moving the fastener holder and/or the fastener closure means toward each other, and means for applying a drive force to one or more fastener pushers so as to drive the fasteners into the closure means.

Also included are tissue release means for pivotally biasing at least one of said fastener holding means and fastener closure means toward a position whereby the space between them generally exceeds the space associated with the initial position, the tissue release means being operable only after the drive force has been applied.

More particularly, the tissue release means includes first means for applying a biasing force to the fastener holder means to pivot the fastener holder into an opened position; second means for initially resisting the biasing force of said first means until the second means moves to a released condition; and third means for releasing said second means in response to both application of drive force along axial drive means and release of the releasable means for moving the fastener holder and/or fastener closure means toward each other.

The first means comprises a wire spring associated with the body of the apparatus, the wire spring having a proximal portion which is fixed to the fastener body, and a movable distal portion which contacts a boss projecting laterally from the fastener holder means, the wire spring exerting a biasing force on said boss.

The second means comprises a leaf member, such as a leaf spring, associated with the body of the apparatus and having a distal portion for contacting the base of the fastener holder. The leaf member permits longitudinal motion of the fastener holder means while preventing pivoting thereof.

The leaf spring applies a biasing force of such magnitude and direction so as to resist the biasing force of said first means.

The third means comprises an elongated flexible strip, preferably fabricated from a polymeric material, which is slidably movable from an initial distal position wherein the elongated member prevents the leaf spring from moving to its released condition, to a proximal position wherein the leaf spring is released and free to move to its released condition. The elongated member also has a longitudinally extending slot.

The axial drive means of the apparatus comprises a thrust bar having a depending member for engaging said slot of the flexible strip, the thrust bar being longitudinally movable from an initial proximal position wherein the depending member is not in engagement with the slot, to a distal position wherein the depending member engages the slot, and the thrust bar being returnable to a final proximal position wherein the depending member moves the flexible strip to its proximal position for releasing the leaf spring. The depending member of the thrust bar preferably has a camming surface for contacting the proximal edge of the flexible strip. The axial drive means can be offset from the axial centerline of movement of the fastener pushing means.

BRIEF DESCRIPTION OF THE DRAWINGS

Preferred embodiments of the invention are described hereinbelow with reference to the drawings wherein:

FIGS. 3, 4, 5, and 6 are exploded perspective views of the fastener applying mechanism of the apparatus;

FIG. 7 is a perspective view of the retainer support arm of the apparatus;

FIG. 8 is a perspective view of the retainer mounting strip of the apparatus;

FIGS. 10, 11, 12 and 13 are elevational views partially cut-away, sequentially illustrating the fastener application with the apparatus of the invention;

FIGS. 14 and 15 are cross-sectional views of the fastener cartridge and anvil assembly, illustrating the operation of the apparatus in prefired and fired conditions, respectively.

DETAILED DESCRIPTION OF THE PREFERRED EMBODIMENTS

Figure 1:
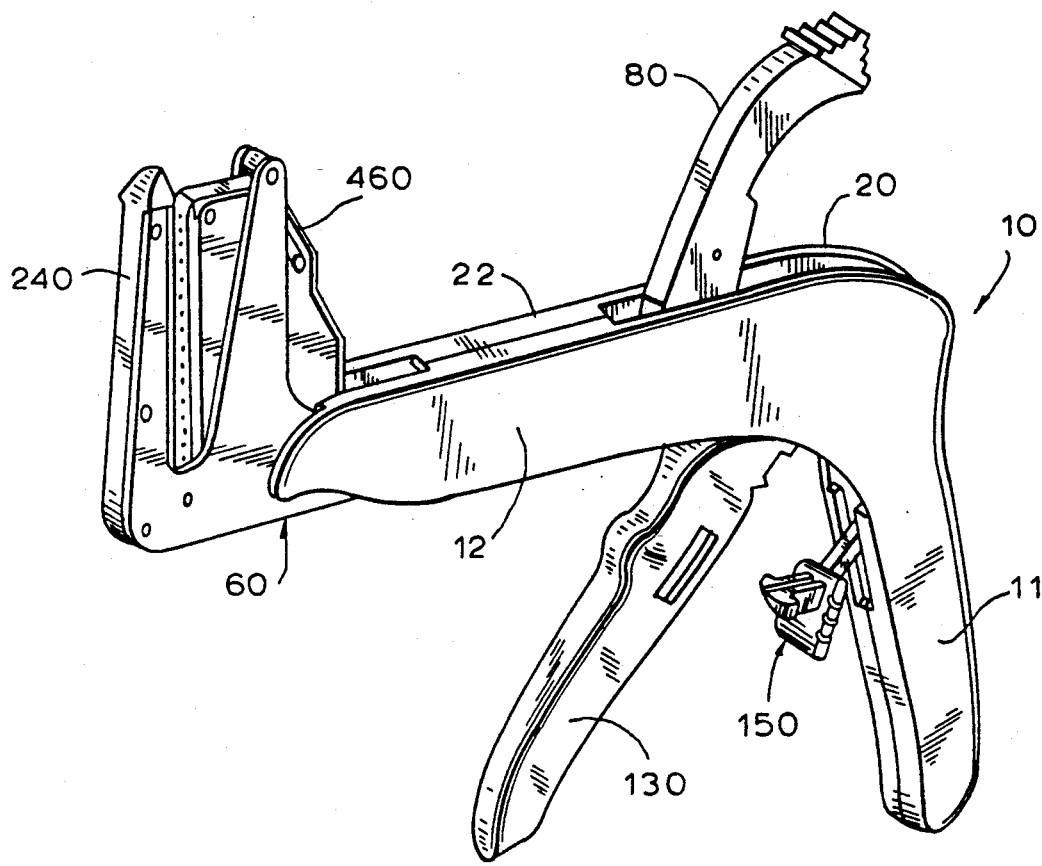
FIG. 1 is a perspective view of the fastener applying apparatus of the present invention.

Referring initially to FIGS. 1 to 4, left and right body portions, 10 and 20 respectively, provide means for housing the actuating mechanism of the invention and also provides means for allowing the user to hold the instrument. Each body portion has a handle portion, 11 and 21 for the left and right body portions respectively, and a longitudinally or axially extending portion 12 and 22, respectively. The body portions also each have internal struts 23 which include recessed portions 23a associated with the internal wall surface of the handle. The struts provide added strength and support. The recessed portions 23a receive and hold the frame extension 50 in a fixed position. Aperture 25 in the right body portion and a corresponding aperture in the left body portion receive trigger pivot pin 140 shown in FIG. 3. Recessed portions 24 and 14 of the right and left body portions from a slot for receiving the pivot arm 151 of safety catch 150.

Figure 3:
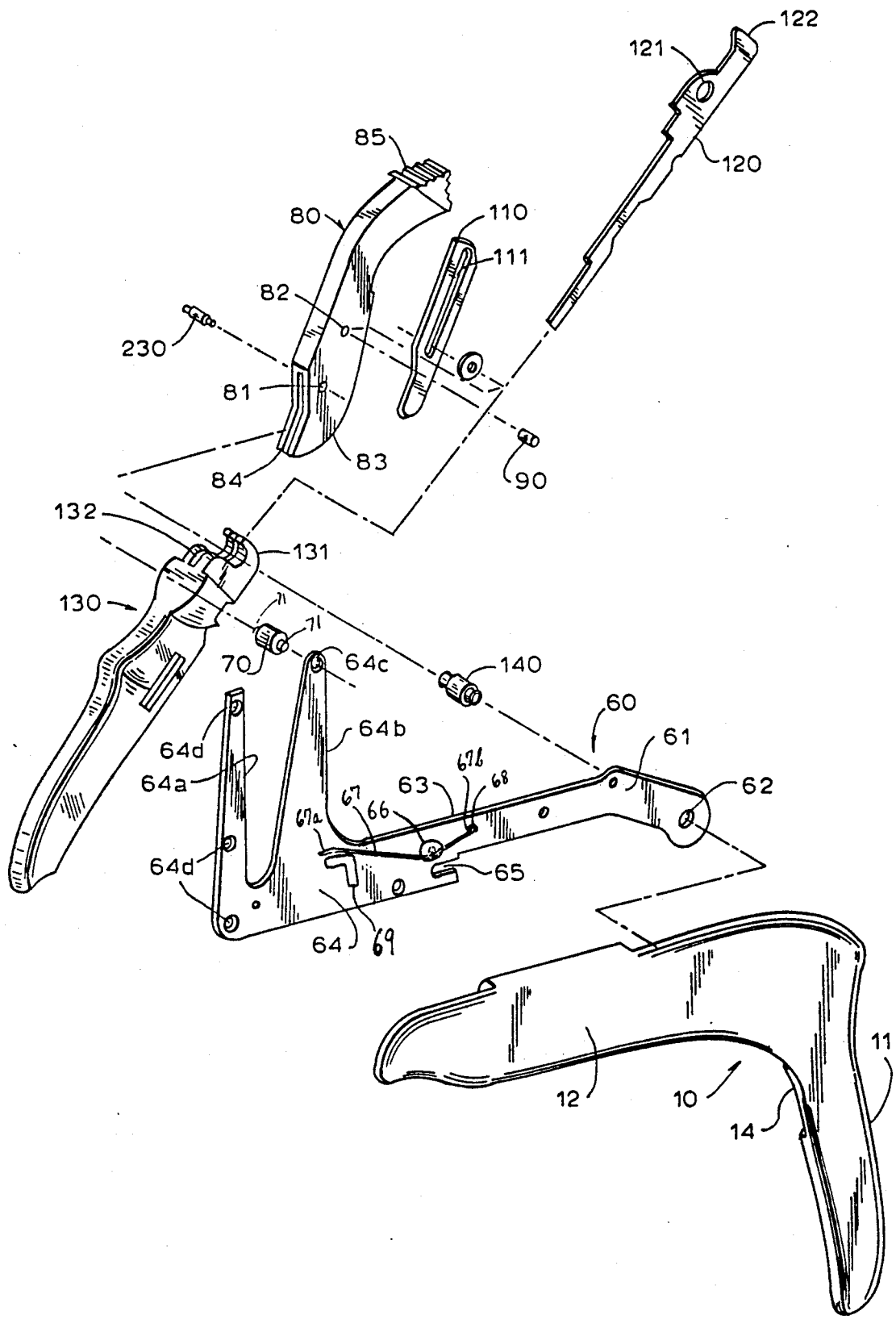

Referring to FIG. 3, left frame 60 is an elongated member having an axially extending longitudinal portion 63; a proximal portion 61 which is inclined from the longitudinal portion and which defines aperture 62 for receiving trigger pivot pin 140; a U-shaped distal portion 64 having a distal leg 64a, a proximal leg 64b, aperture 64c for receiving shoulder rivet 70, and apertures 64d for receiving rivets 250 for mounting to the retainer housing 240 (see FIG. 6); and notch 65 for engaging one of the detents 211 of the spring retainer 210.

Figure 3A:
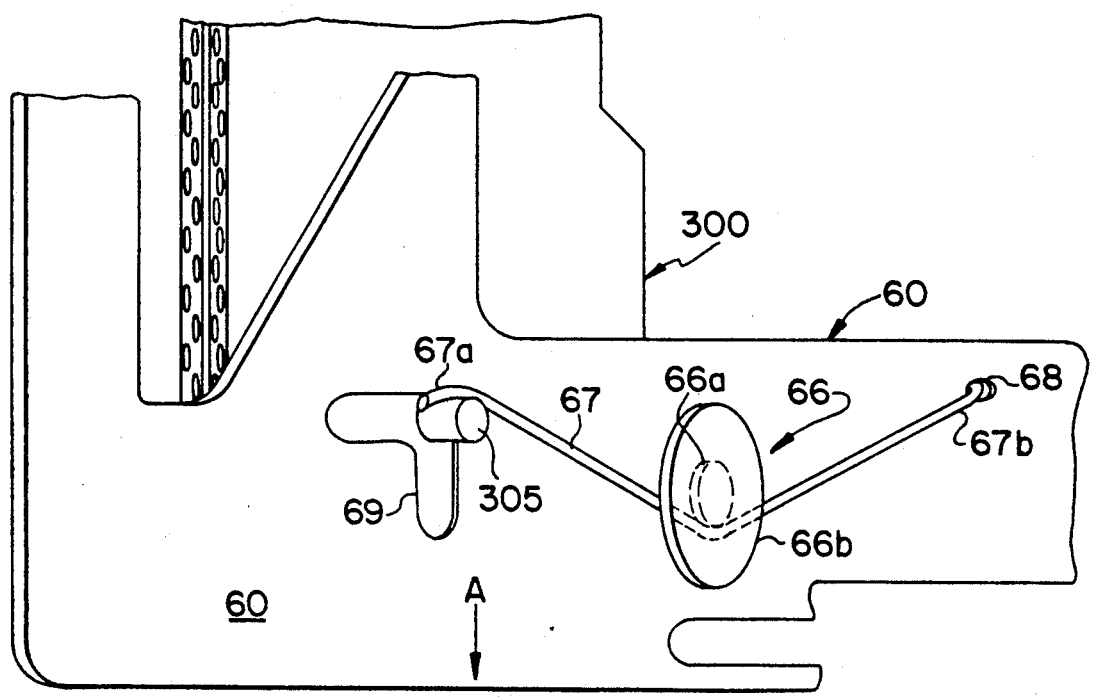
FIG. 3A is a perspective view showing the wire spring of the present invention.

Referring to FIG. 3A, the left frame 60 also has a fulcrum button 66 projecting outwardly from the side thereof. A biasing wire spring 67, which is preferably a resilient metal rod, contacts the inner member 66a of the fulcrum button 66. Relatively wider outer member 66b helps to retain the spring 67. The proximal end 67b of the biasing wire spring is fixed to the left frame, preferably by being inserted into an aperture 68 to prevent said proximal end 67b from moving. The distal end 67a of the spring is resiliently movable and is positioned over boss 305 of side plate 300 of the fastener holding cartridge 460. Boss 305 projects through slot 69 of the left frame. The wire spring 67 exerts a downward biasing force on boss 305 in the direction shown by arrow A. The biasing force urges the fastener holding cartridge 460 to pivot in the open position. The biasing force of wire spring 67 opposes the biasing force of leaf spring 220 shown in FIG. 4, but it is not sufficient to overcome the leaf spring biasing force. Therefore, the biasing force of wire spring 67 becomes effectual only after leaf spring 220 is released, as explained below. When the fastener holder is released into the open position after the instrument is fired, it will separate from body tissue quickly.

While the wire spring 67, fulcrum 66, slot 69, and boss 305 are illustrated in association with the left frame 60, it is also within the scope of the present invention to provide such features on the right frame 30 as an alternative or in addition to the left frame 60.

Figure 6:
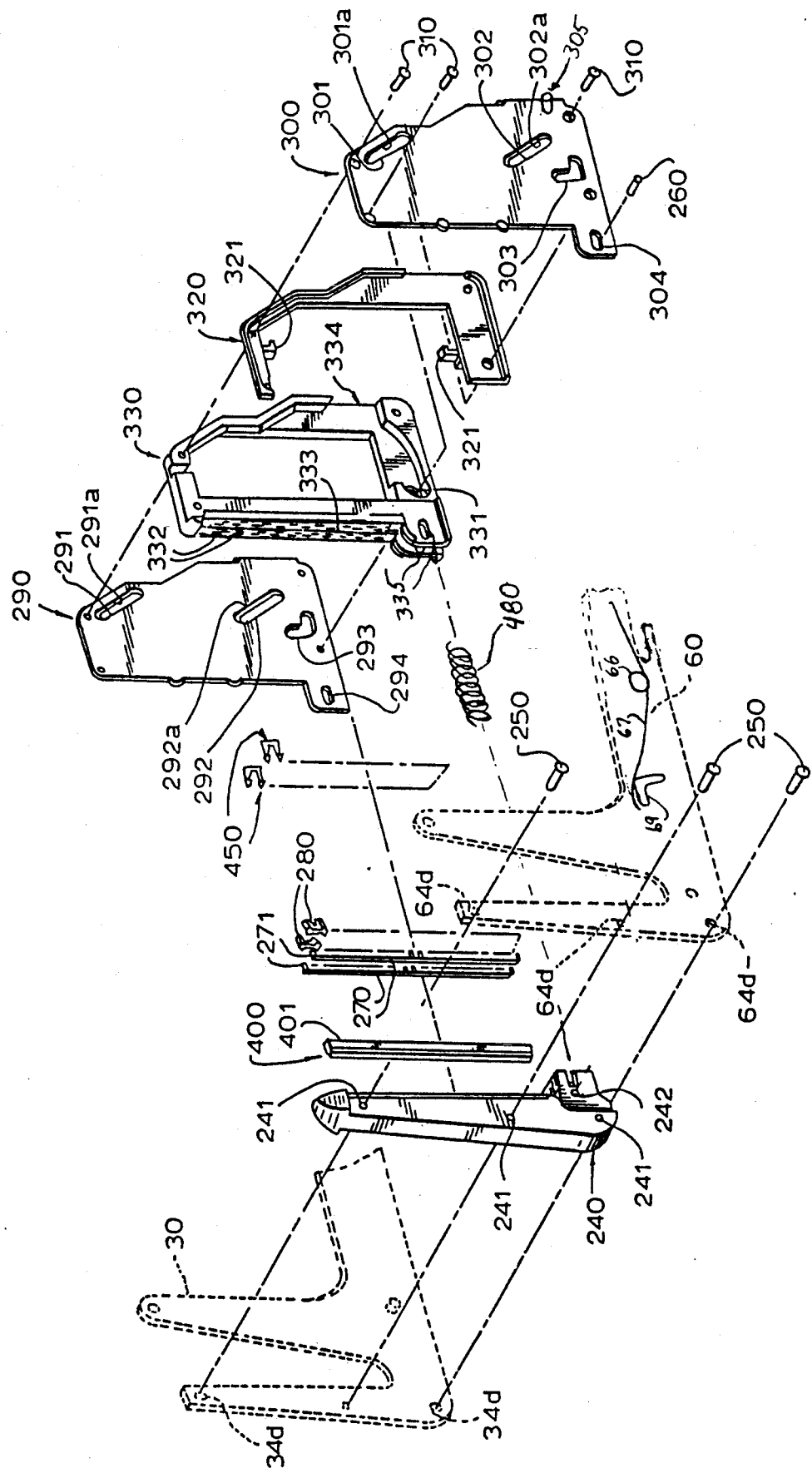

Referring now to FIG. 4, right frame 30 is an elongated member having an axially extending longitudinal portion 33; a proximal portion 31 which is inclined from the longitudinal portion and which possesses an aperture 32 for receiving trigger pivot pin 140; a U-shaped distal portion 34 having a distal leg 34a, a proximal leg 34b, aperture 34c for receiving shoulder rivet 70, and apertures 34d for receiving rivets 250 for mounting to the retainer housing 240 as shown in FIG. 6; and notch 35 for engaging one of the detents 211 of the spring retainer 210 as shown in FIG. 4. Additionally, right frame 30 is fixedly mounted to frame extension 50 such that both have aperture 32 in common. Frame extension 50 has an indentation 51 on its distal edge for accommodating the pivot arm 151 of safety latch 150.

Referring now to FIG. 6, left and right frames 60 and 30, respectively, are mounted in a parallel spaced apart relationship to each other. The distal U-shaped portions define the U-shaped distal end of the instrument. The mutually facing surfaces of the distal portions of the frames are flat thus eliminating intermediate components and facilitating improved component alignment and minimizing dimensional tolerance variations. This is in contrast to prior art instruments in which similarly shaped distal plates possessed inward indentations or jogs to demarcate the distal leg which supported an anvil assembly of lesser width than the fastener holder. In the prior art instruments (see e.g. U.S. Pat. No. 4,665,916) alignment of fastener components and body tissue was provided by a longitudinally mounted alignment pin which pierced the body tissue being fastened. In the present invention alignment is facilitated by the provision of closer tolerances between the flat inner sides of the frames and the fastener holder, by spacer pin 70 which maintains a predetermined distance between the ends of proximal legs 64b and 34b, and through the use of a material of construction for the frames which ensures that the frames will neither deform nor fatigue during use. Preferably, the frames are constructed from stainless steel having a thickness of at least 0.07 inches and preferably of from 0.07 to 0.08 inches. Parallelism and close tolerances are thereby maintained for proper alignment of the fastener holder with the anvil.

Figure 2:
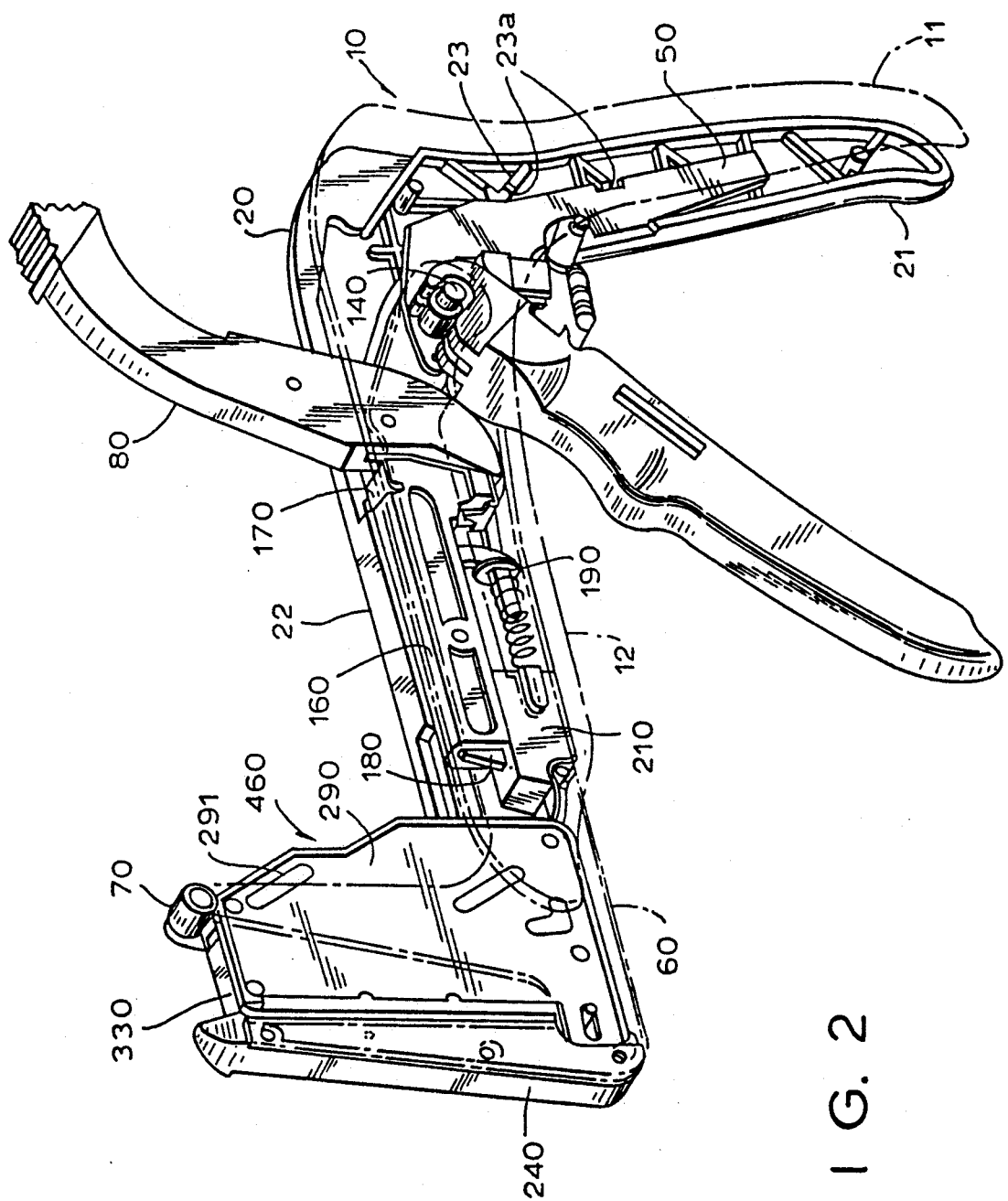
FIG. 2 is a perspective cut-away view of the apparatus of the present invention.

In FIGS. 2, 3, and 4, spacer pin 70 extends laterally between the proximal legs 64b and 34b of the left and right frames, and projections 71 are received into apertures 64c and 34c. Spacer pin 70 spaces the left and right frames apart at a fixed predetermined distance and serves as a guide for the fastener holding cartridge.

Referring to FIGS. 2 and 3, actuator 80 serves as part of the fastener cartridge actuation means, i.e. it is an approximating means to move the fastener cartridge from a proximal open position such that body tissue can be freely inserted into the gap between the fastener cartridge and the anvil assembly, into a distal closed position wherein it can hold body tissue clamped between it and the anvil assembly, as discussed below. Actuator 80 is a lever pivotally mounted to the left and right body portions 10 and 20 by means of a pin 230 disposed through aperture 81. Aperture 82 receives pin 90 for mounting lever rod 110. Actuator 80 has a forked distal end 83 and a longitudinal central slot 84. Thumb rest 85 is at the proximal end.

Lever rod 110 is an elongated member defining longitudinal central slot 111. Lever rod 110 is slidable mounted within slot 84 of the actuator by means of pin 90 disposed through aperture 82, washer 100 and slot 111.

Trigger 130 is an elongated lever arm having a forked end with curved hook-like members 131 shown in FIG. 3. Central slot 132 extends longitudinally along the underside of the trigger 130. Side slots 133 are provided for engaging the snap prongs 154 of the safety catch 150. Central slot 132 is provided in trigger 130 for receiving trigger insert 120, which is mounted therein. Trigger insert 120 has an aperture 121 which is aligned with the curved hook-like members 131 such that trigger pivot pin 140 is received therethrough. Trigger insert 120 has an end with projection 122 for contacting the proximal end of lever rod 110.

Referring once again to FIGS. 3 and 4, trigger pivot pin 140 is transversely mounted with left and right ends fixed respectively in apertures 25 in the interior surfaces of the left and right portions 10 and 20, and is disposed respectively through apertures 62, 121 and 32, of the left frame, trigger insert and right frame.

Figure 11:
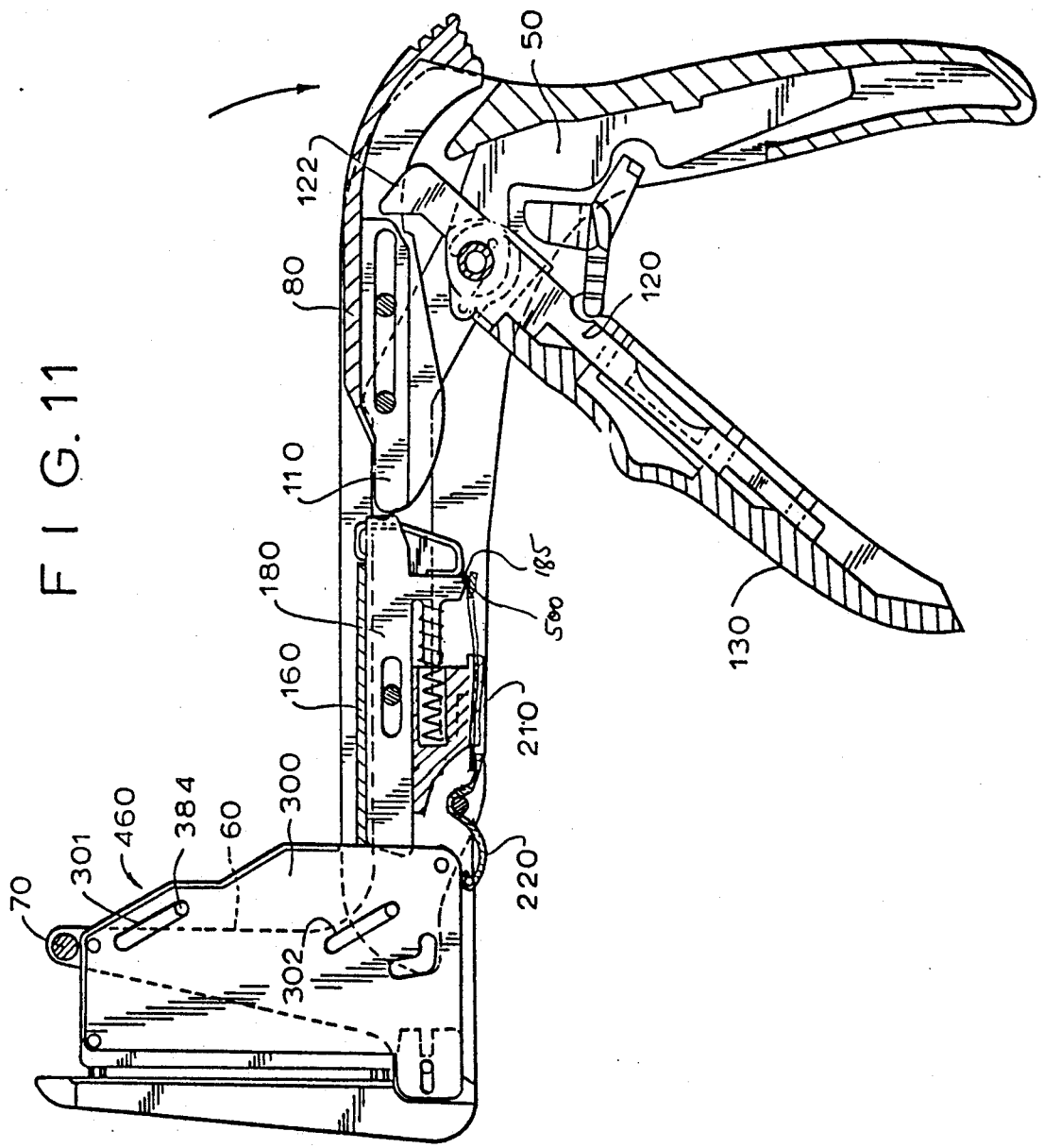

Referring to FIGS. 4, 10 and 11, clamp 160 is an elongated member with longitudinal central slot 161. Cap 170 is mounted on the proximal end of clamp 160 with vertical slot 171 of the cap being aligned with longitudinal slot 161 of the clamp to permit passage therethrough of lever 110. Cap 170 preferably has a sloped proximal surface 172 for being contacted by the forked end 83 of the activator. Clamp 160 has a transversely extending aperture 162 for receiving clamp pin 90.

Thrust bar 180 is an elongated member which is slidable mounted within slot 161 of the clamp. Thrust bar 180 has a longitudinal slot 181 through which clamp pin 90 is disposed. Proximal end 183 is for contacting the distal end of lever 110. Distal edge 184 is for contacting the cam assembly discussed below and is preferably inclined to facilitate camming action between it and link 340. Thrust bar 180 has a distally projecting post 182 for mounting a washer 190 and coiled spring 200. Downwardly projecting member 185 contacts and engages the retainer strip 500 as explained more fully below. The bottom edge of member 185 is preferably inclined to facilitate camming action between it and the proximal edge of retainer strip 500.

Spring retainer 210 is a block shaped piece having longitudinally extending detents 211 for engaging slots 65 and 35 in the left and right frames. The proximal end 212 serves as a backstop for spring 200 such that spring 200 biases the slidable thrust bar 180 in the proximal direction. The distal end has a curved portion 213 for receiving a leaf spring 220.

Retainer pin 231 extends transversely across the underside of the leaf spring 220 and is fixed at its ends in corresponding apertures in the body portions.

A novel feature of the present invention is the use of a slidable retainer strip 500, shown for example in FIG. 4. Retainer strip 500 is mounted within slot 214 of the spring retainer block 210, and is slidably movable in the longitudinal direction. Retainer strip 500 is preferably fabricated from a flexible, resilient material such as polymeric material. The retainer strip 500 possesses a longitudinally extending aperture 501 in proximity to its proximal end. When the instrument is in its initial, pre-fired position, the distal end of the retainer strip 500 extends beyond the distal end of the slot 214 and retains proximal end 221 of leaf spring 220 by forming a shelf upon which proximal end 221 presses. See e.g., FIG. 10. When retainer strip 500 is moved proximally its distal end is withdrawn from support of proximal end 221, thereby releasing the leaf spring 220. This will be discussed in greater detail below.

Figure 5:
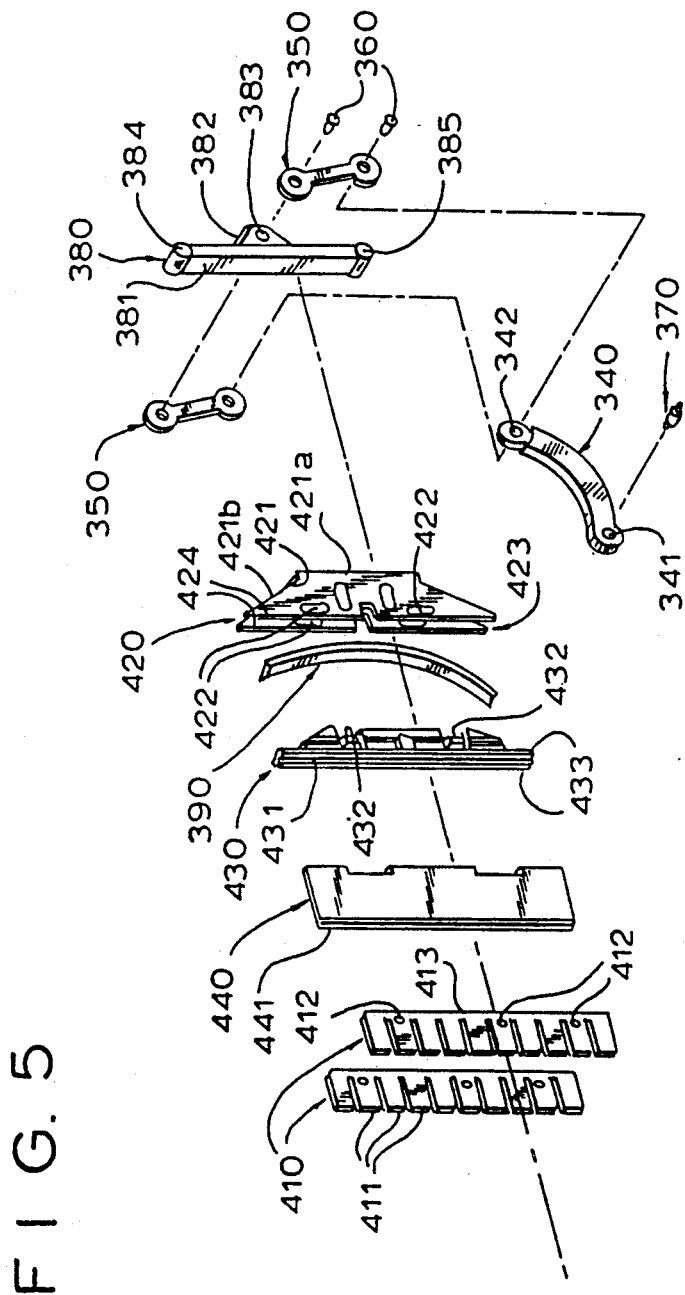

Referring additionally to FIGS. 5 and 6, the fastener holder 460 of the present invention is an assembly which includes several unique features.

The cam assembly, which is housed within the fastener holder 460, is a non-torquing force diverter comprising an assembly of links and a cam plate which converts the off-centered axial drive force to a balanced linear drive force uniformly distributed across the proximal end of the knife blade assembly. With such means for providing this conversion, the need to provide an off-centered drive force directly to the knife assembly is avoided. Such last mentioned force application method would result in unbalanced force and unwanted torque which would pivot and jam the knife and fastener pushers. Moreover, in the present invention, force transmissions and conversions are provided through compression members thereby facilitating definitive and accurate force transmission and conversion. Furthermore, tension cables or the like as utilized in prior developments are avoided.

Referring to FIG. 5, the cam assembly includes curved link 340 having a distal end pivotally mounted in socket 331 in the fastener cartridge 330 by means of pin 370 disposed through aperture 341. The proximal end of link 340 is pivotally attached by a pin 360 to one end of an intermediate link 350. The other end of the intermediate link 350 is pivotally attached by a pin 360 to cam bar 380. Cam bar 380 has a flat distal camming surface 381, a rear projection 382 with aperture 383 for receiving a pivot pin 360, and upper and lower bolts 384 and 385 which project into and ride along the inclined slots 291, 292, 301, and 302 of the right and left side plates. The flat distal camming surface 381 of the cam bar is for contacting the proximal surface 421a of the back of the blade channel 420.

The movement of the cam bar has a vector component linearly aligned with the path of movement of the fastener pushers 410, knife 440, and blade channel 420. Unaligned components of motion are not transmitted to the blade channel 420 because the cam bar's distal surface 381 remains in a perpendicular orientation relative to the center line of movement of the fastener pushers 410 and blade channel 420, and because the camming surface 381 is slidable relative to proximal surface 421a.

Referring once again to FIG. 5, the knife blade assembly also housed within the fastener holder 460, includes blade channel 420, leaf spring 390, blade holder 430, and knife blade 440.

Blade channel 420 has two parallel dovetail shaped portions 424 projecting distally from a back portion 421. The dovetail portions define apertures 422 for engaging projections 432 of the blade holder 430. Together, dovetail portions 424 define a channel 423 in which leaf spring 390 is located. The back portion 421 has a proximal surface 421a for contacting the distal camming surface 381 of the cam bar, and a distal surface 421b which is contacted by leaf spring 390.

Curved leaf spring 390 is located between the blade holder 430 and the blade channel 420. Its ends are retained by inwardly projecting stubs 321 of the cartridge cap 320. Spring 390 contacts the distal surface 421b of the back of the blade channel 420, thereby biasing the blade channel 420 proximally.

The distal end of blade holder 430 has a slot 431 for mounting a knife blade 440. Projections 432 on the sides of the blade holder are mounting fixtures received into apertures 422 of the blade channel.

Knife blade 440 has a sharp distal edge 441 for cutting body tissue. The proximal edge of blade holder 430 shown in FIG. 5 is mounted in slot 431 of the blade holder.

Referring once again to FIG. 5, cartridge pushers 410 are substantially flat strips having distal pointing finger-like projections 411 for pushing the fasteners through slots 332, and out of the cartridge 330 into engagement with their respective retainers 280 in the anvil assembly. At lease one side of each pusher possesses an interference means, such as one or more detents 412, which frictionally engage the surface 335 of the corresponding slot in the fastener cartridge 330 in which the pusher slides. (See FIG. 15.) These detents advantageously prevent the pushers from retracting once they have been moved to their most distal position, thereby preventing the fasteners from migrating or deflecting back into slots 332. Such migration or deflection, if unimpeded, may result in non-engagement of the fastener with its corresponding retainer The proximal edges 413 are contacted by surfaces 433 of the blade holder such that when the blade holder is moved distally, surfaces 433 urge the fastener pushers 410 towards the distal direction.

Referring to FIG. 6, fastener holder 460 also comprises cartridge member 330 having a plurality of fastener slots 332, a knife slot 333, a rear slot 334 through which the distal end 184 of the thrust bar enters, and socket 331 for retaining distal end 341 of the curved link. Elongated slot 335 receive pin 260 and allows the fastener holder 460 to be both pivotally and longitudinally movable with respect to the anvil assembly support arm 240. Compression spring 480, which is mounted between the anvil assembly support arm 240 and the fastener holder 460, exerts a longitudinal biasing force to maintain the fastener holder 460 in a proximal position. This biasing force is overcome when the instrument is actuated by pressing lever 80. The fastener holder 460 therefore exhibits a linear or longitudinal motion and a pivotal motion with respect to the anvil assembly support arm 240. Pivotal biasing forces are exerted upon the fastener holding cartridge 460 by wire spring 67 and leaf spring 220, as explained infra.

It should be noted that the initial configuration of the jaws of the apparatus is such that the tissue contacting surface of the fastener holder 460 is biased by leaf spring 220 to a generally parallel spaced apart relation to the tissue contacting surface of the anvil arm 240. The predetermined clearance or gap space between the two surfaces allows body tissue, such as uterine wall tissue, to be positioned within the gap space. The leaf spring 220 maintains a biasing force to keep the two above-mentioned surfaces in contact with the body tissue, thereby reducing the possibility of having extraneous body tissue enter the gap.

Cartridge cap 320, which is mounted to cartridge 330, has inwardly projecting stubs 321 for retaining the ends of the leaf spring 390.

Left and right side plates 300 and 290 respectively each have two inclined slots (301 and 302 in side plate 300; 291 and 292 in side plate 290) for retaining the bolts 384 and 385, which are slidable received therein. Said slots are defined by guide surfaces (301a, 302a, 291a, 292a, respectively) which contact the circumferential surfaces of the respective ends of the bolts disposed therethrough and restrain the movement of the bolts to a predetermined linear path. The width of the slots 301, 302, 291 and 292 closely match the width of the respective bolts 384 and 385 while leaving enough clearance for free sliding of the bolts. Slots 304 and 294 receive cartridge pivot pin 260, which pivotally mounts the fastener holder 460 to the frame. Slots 303 and 293 receive bosses 36 of the inner sides of the respective frames. Pins 310 are disposed respectively through apertures in the left side plate 300, the cartridge cap 320, the cartridge 330, and the right side plate 290.

The anvil assembly comprises retainer support arm 240, anvil block 400, retainer holding strips 270, and retainers 280. Arm 240 is mounted between the distal arms 64a and 34a of the frames by means of pins 250 disposed through corresponding apertures 241 in the arm 240, and apertures 64d and 34d in the frames. Aperture 242 in the arm receives cartridge pivot pin 260. In other embodiments, the anvil assembly can include a means for replacing retainers (for example in reusable/reloadable instruments), or crimping means (for example, with metal staples).

Figure 9:
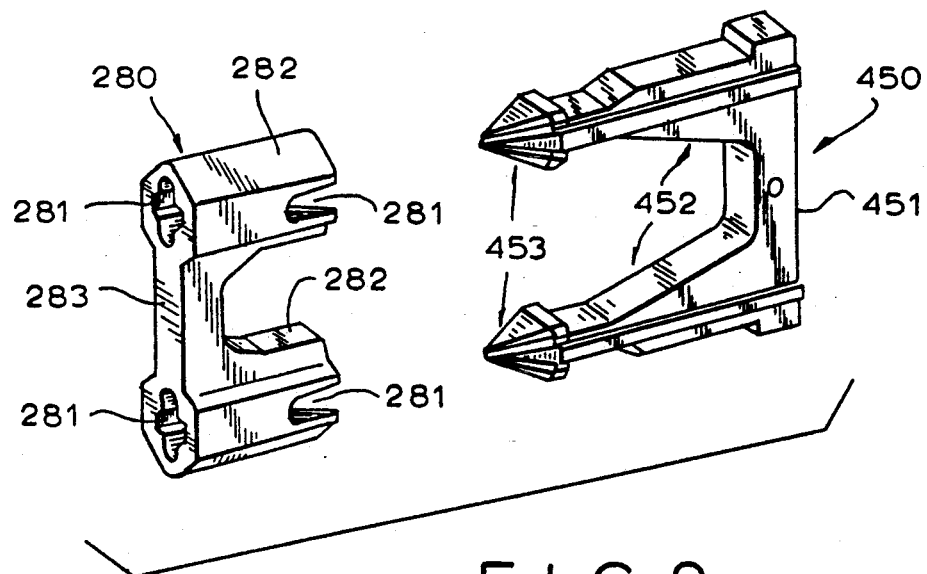
FIG. 9 is an enlarged perspective view of a two part surgical fastener which can be applied to body tissue by means of the apparatus of the present invention.

Referring additionally now to FIG. 9, two-part bioabsorbable surgical fasteners useful in the present invention generally comprise a fastener portion 450 having a backspan 451, and prongs 452 with barbs 453 at the tips thereof. The fasteners are initially located in slots 332 of the cartridge. When the pusher members 410 are distally moved, the finger-like projections 411 each contact the backspan 451 of a fastener 450, thereby moving it through and out of its respective slot 332. The retainer portion 280 of the two-part fastener comprises a base 283 with columnar members 282 having apertures 281 for receiving the barbed prongs 452 of the fastener. Once engaged, the fastener and the retainer lock together, hence the desirability of constructing them of bioabsorbable material such as polyglycolide, polylactide or copolymers thereof for suturing body tissue.

Referring again to FIG. 6 and additionally to FIGS. 7 and 8, retainers 280 are preferably mounted on retainer mounting strips 270 in arm member 240 such that each retainer is aligned with a corresponding fastener portion in the respective fastener slots 332. Mounting strip 270 includes a plurality of mounting posts 271 each of which frictionally engages a respective aperture 281 of the retainer. Mounting strip 270 also includes projections 273 which ride in a corresponding slot in retainer support arm 240, and which serve as a limiter to prevent lateral sliding of the mounting strip. Hook-shaped catches 272 snap into windows 243 of the retainer support arm 240 thereby preventing the retainer mounting strips 270 from dropping out of the support arm 240. Mounting strip 270 is thus adapted to be loaded with retainers prior to its introduction into retainer support arm 240. This external retainer-loading feature of mounting strip 270 is particularly advantageous because the retainers are typically quite small, e.g., about 0.2 inches in length, and are therefore difficult to handle. Mounting strip 270 permits retainers to be conveniently mounted onto mounting posts 271 and then the entire mounted assembly is easily snapped into retainer support arm, mounting fresh retainers, and repositioning within retainer support arm 240.

Preferably, at least two rows of retainers 280 are mounted in arm 240. The rows are separated by an anvil block 400 which provides a means for contacting body tissue and providing a backstop surface for the cutting edge 441 of the knife. when the barbed prongs 452 enter the top of the column members 282, the posts 271 are pushed out of the opposite end of the aperture 281 by the entering barb 453, and thereby disengage the retainer 280, releasing it from the anvil assembly.

Referring to FIGS. 10 to 13, the instrument is initially in the open and unfired condition illustrated in FIG. 10. In the initial condition of the instrument, retainer strip 500 is located in slot 214 of the spring retainer block 210. The distal end of the retainer strip 500 extends beyond the distal end of slot 214 and is positioned so as to retain proximal end 221 of spring 220. The proximal end of the retainer strip 500 extends beyond the proximal end of slot 214 to permit member 185 of the thrust bar to contact the retainer strip 500 and engage aperture 501 when the instrument is fired. For use in surgical operations the instrument is positioned by the surgeon such that the body tissue to be fastened is located in the U-shaped distal portion between the jaws of the instrument, i.e. in the gap between the fastener holder 460 and the anvil assembly. Leaf spring 220 biases the fastener holder to an initial position whereby the fastener holder is in parallel spaced apart relation to the anvil assembly. The gap between them is of predetermined spacing so as to accommodate the body tissue to be operated upon. Extraneous tissue is excluded because the fastener holder 460 is biased so as to maintain contact with the body tissue, thereby leaving no extra room in the gap for extraneous tissue.

The surgeon then actuates the instrument: by pivoting actuator or approximating lever 80 down (i.e. clockwise as shown) from the position shown in FIG. 10 to the position shown in FIG. 11. By this movement, the fastener holder 460 will move distally to a closed position wherein it contacts the body tissue (not shown) to secure the body tissue in a fixed position. Moving the actuator lever 80 down also moves the clamp 160 forward and aligns lever 110 along the longitudinal axis of the instrument. The distal end of clamp 160 contacts the fastener cartridge 460 and moves it linearly from the initial position to a closed position. It should be noted that until lever 110 is aligned, the fasteners cannot be fired.

The instrument at this point is in the condition illustrated by FIGS. 11 and 14. The next step for the surgeon is to release the safety catch 150 by pivoting it down (counter-clockwise as shown), thereby putting the instrument in a "ready to fire" condition.

To fire the instrument, the surgeon pivots the trigger lever 130 (counter-clockwise as shown) by manual application of a proximally directed force. This movement, in turn, pivots trigger insert 120 and converts the proximally directed force to a distally directed force such that portion 122 moves lever 110 distally. Lever 110 pushes the thrust bar 180 distally, and thrust bar 180 presses on link 340. This motion is transferred by link 350 to cam bar 380. Cam bar 380 has a path of movement defined by slots 291, 292, 301, and 302, all of which are aligned in the same predetermined direction.

Referring to FIG. 11, it can be seen that when the instrument is being fired member 185 of the thrust bar moves distally. The sloped bottom edge of member 185 allows it to contact the proximal end of the retainer strip 500 and by a camming action, to move it aside.

The blade channel 420 is moved forward by the cam bar 380 and surface 433 pushes the fastener pushers distally, thereby driving the fasteners out of the slots, and into the retainers. Detents 412 on the fastener pushers 410 frictionally engage the surface 335 of their respective slots in cartridge 330. This frictional engagement prevents the fastener pushers from returning to their proximal position after they have been moved to their distal position. Knife blade 440 is moved distally through slot 333 thereby cutting any body tissue 470 (shown in FIG. 15) between the knife and the anvil block 400 which the knife edge 441 impinges. The instrument thereby creates an incision into body tissue which is sealed by a row of fasteners on each side.

The prongs 154 of the safety catch snap into locking engagement with slots 133 of the trigger and thereby prevent inadvertent firing of an unloaded instrument.

Figure 12:
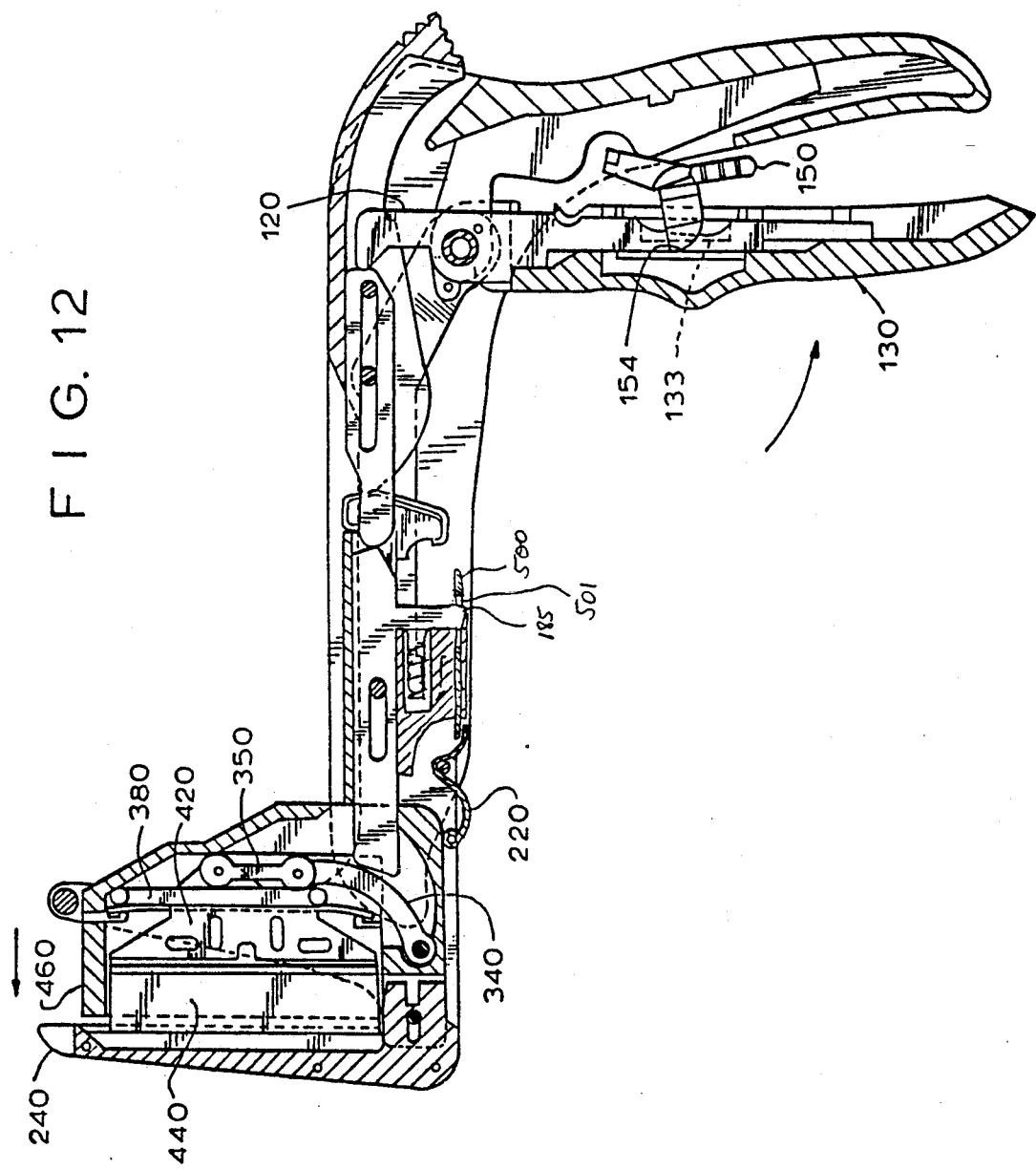

The instrument is now in the fired position illustrated by FIGS. 12 and 15.

As can be seen in FIG. 12, when the instrument is fully fired, member 185 has moved to its most distal position and has engaged aperture 501 of the retainer strip.

Figure 13:
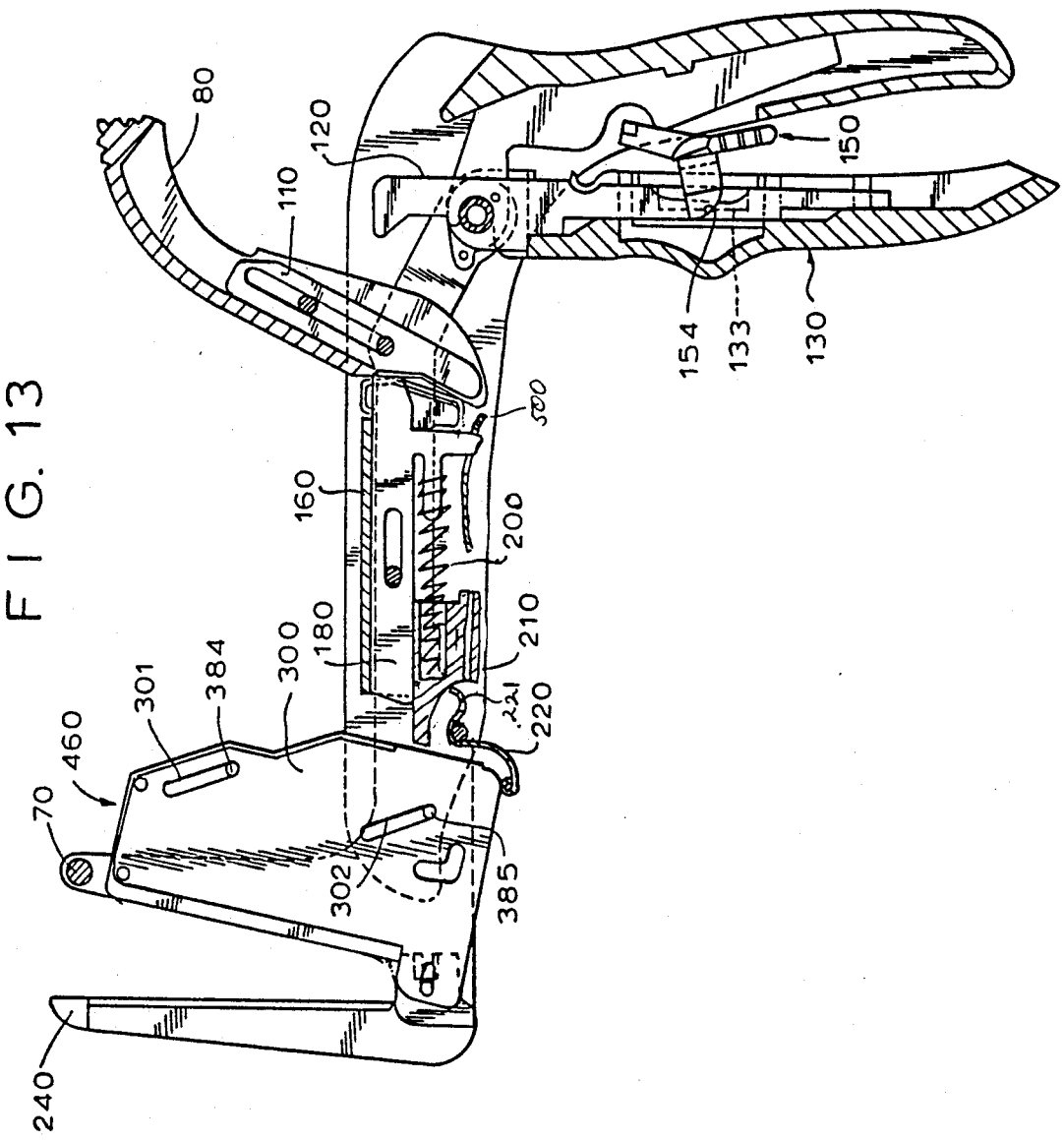
Figure 16:
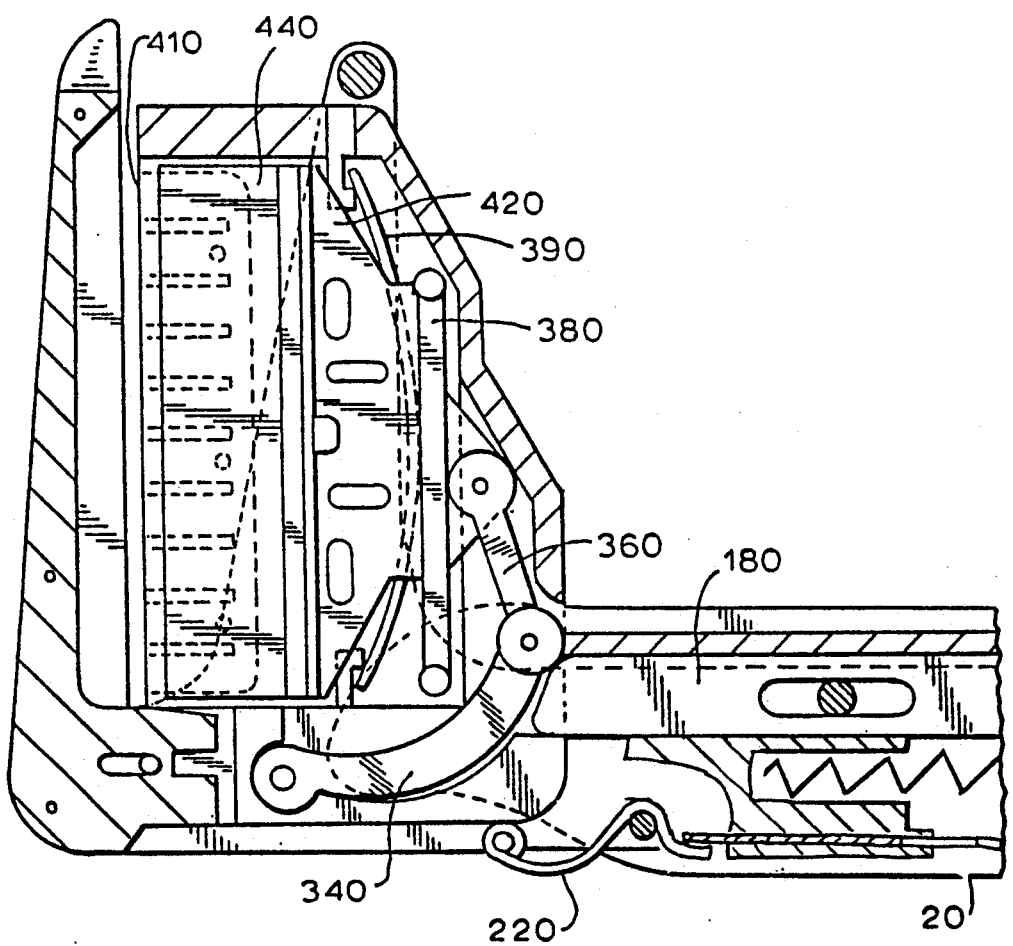
FIG. 16 is an elevational cut-away view of the fastener cartridge and anvil assembly after the apparatus has been fired.

Referring now to FIGS. 13, 15 and 16, to open the instrument and release the body tissue, the surgeon pivots the actuator lever 80 counterclockwise into the upward or released position as shown in FIG. 13. The knife assembly, being biased proximally by spring 390, retracts into the fastener holder 460. The fastener holder 460 moves back to a proximal position. The thrust bar 180 and clamp 160 return to their proximal position because of the biasing force of spring 200.

Member 185 of the thrust bar pulls the retainer strip 500 proximally, thereby releasing proximal end 221 of leaf spring 220. At this point leaf spring 220 can no longer exert a biasing force on the fastener cartridge 460. Up to this point, the biasing force of wire spring 67, shown in FIG. 3A, was not sufficient to overcome the biasing force of spring 220. However, when leaf spring 220 is released as described above, the biasing force of wire spring 67 quickly pivots the fastener cartridge 460 into a fully open final position. The gap space between the fastener holder 460 and the anvil assembly support arm 240 is greater in the fully opened final position than the gap space in the initial prefired position. This feature allows easy release of tissue after the instrument has been fired, while retaining the benefit of the controlled gap space in the prefired condition. In the preferred embodiment described herein, the initial motion of the fastener cartridge 460 is linear in the distal-proximal direction. The movement of the fired fastener cartridge to its final position is pivotal. However, other motion paths are also possible.

The instrument can be made of any size suitable for its purpose of fastening body tissue, and the various parts can be made of materials appropriate to their function. For example, the body, actuator lever, and trigger can be injection molded from a high strength polymer. The frames, cam assembly, fastener pushers, and blade channel can be constructed from an appropriate metal.

The instrument has application in a full range of surgical applications including abdominal, gynecological, pediatric, and thoracic surgery for resection and transection. In a preferred embodiment, the instrument includes bioabsorbable fasteners and retainers and has application in the creation of a temporary opening such as hysterotomy, to align the tissue layers and minimize bleeding during a cesarean delivery.

While the above description contains many specific details, these details should not be construed as limitations of the scope of the invention, but merely as examples of preferred embodiments thereof. Those skilled in the art will envision many other possible variations that are within the scope and spirit of the invention as defined by the claims appended hereto.

What is claimed is:

1. Apparatus for applying a plurality of surgical fasteners to body tissue or the like by gripping body tissue between fastener holding means and fastener closure means, applying the fasteners to the body tissue, and closing the fasteners, which comprises means for pivotally biasing at least one of said fastener holding means and said fastener closure means toward a position which provides separation of the body tissue from said fastener holding means and fastener closure means, and means for resisting the force of said pivotal biasing means, said resisting means being disengaged after the fasteners have been closed.

2. Apparatus for applying a plurality of surgical fasteners to body tissue or the like, which comprises:
body means;
fastener closure means at one end portion of said body means for providing closure of surgical fasteners;
fastener holding means mounted relative to said fastener closure means, said fastener holding means being adapted for holding a plurality of surgical fasteners;
at least one of said fastener holding means and fastener closure means being biased toward a first spaced position for reception of body tissue or the like therebetween, whereby the body tissue is contacted by said fastener holding means and said fastener closure means;
means for moving at least one of said fastener holding means and fastener closure means toward the other to a second position sufficient to clamp the body tissue positioned therebetween;
means for moving the surgical fasteners toward said fastener closure means to effect closure of the surgical fasteners;
means for pivotally biasing at least one of said fastener holding means and fastener closure means toward a position which provides separation of the tissue from said fastener holding means and said fastener closure means, and means for resisting the force of said biasing means, said resisting means being disengaged after said surgical fasteners have been moved to effect closure.

3. Apparatus for applying a plurality of surgical fasteners to body tissue or the like, which comprises:
body means;
fastener closure means at one end portion of said body means for providing closure of surgical fasteners;
fastener holding means mounted relative to said fastener closure means, said fastener holding means being adapted for holding a plurality of surgical fasteners;
at least one of said fastener holding means and fastener closure means being biased toward a first spaced position for reception of body tissue or the like therebetween, whereby the body tissue is contacted by said fastener holding means and said fastener closure means;

means for moving at least one of said fastener holding means and fastener closure means toward the other to a second position sufficient to clamp the body tissue positioned therebetween;

means for moving the surgical fasteners toward said fastener closure means to effect closure of the surgical fasteners; and means for biasing at least one of said fastener holding means and fastener closure means toward a position whereby the space therebetween exceeds the spaced associated with said first position, whereby the force of said biasing means is resisted by resisting means which is disengaged after said surgical fasteners have been moved to effect closure.

4. The apparatus of claim 3 wherein said fastener body means has a longitudinal portion enclosing an axial drive means for transmitting said drive force.

5. The apparatus of claim 4 wherein said means for moving the surgical fastener includes an axial drive means and at least one fastener pushing member having a centerline of movement offset from said axial drive means.

6. The apparatus of claim 4 wherein said means for biasing at least one of said fastener holding means and fastener closure means comprises:

first means for applying biasing force to said fastener holding means to pivot said fastener holding means into an opened position;

second means for initially resisting the biasing force of said first means until said second means moves to a released condition; and third means for releasing said second means in response to both application of said drive force along said axial drive means and return of said fastener holding means to its proximal position.

7. The apparatus of claim 6 wherein said first means for applying biasing force comprises a wire spring associated with the body of the apparatus, said wire spring having a proximal portion which is fixed to the fastener body, and a movable distal portion which contacts a boss projecting laterally from the fastener holding means, said wire spring exerting a biasing force on said boss.

8. The apparatus of claim 6 wherein said second means for initially resisting the biasing force comprises a leaf member associated with the body of the apparatus and having a distal portion for contacting the fastener holding means, said leaf member permitting longitudinal motion of the fastener holding means while preventing pivoting thereof.

9. The apparatus of claim 8 wherein said leaf member comprises a leaf spring with a distal portion in contact with the base of said fastener holding means, said leaf spring applying a biasing force of such magnitude and direction so as to resist the biasing force of said first means.

10. The apparatus of claim 6 wherein said third means for releasing said second means comprises an elongated member which is slidably movable from an initial distal position wherein said elongated member prevents said second means from moving to said released condition, to a proximal position wherein said second means is released and free to move to its released condition.

11. The apparatus of claim 10 wherein said elongated member comprises a flexible strip having a longitudinally extending slot.

12. The apparatus of claim 11 wherein said flexible strip is fabricated from a polymeric material.

13. The apparatus of claim 11 wherein the axial drive means comprises a thrust bar having a depending member for engaging said slot of said flexible strip, said thrust bar being longitudinally movable from an initial proximal position wherein said depending member is not in engagement with said slot, to a distal position wherein said depending member engages said slot, and said thrust bar being returnable to a final proximal position wherein said depending member moves said flexible strip to its proximal position for releasing said second means.

14. The apparatus of claim 13 wherein said depending member of said thrust bar has a camming surface for contacting the proximal edge of said flexible strip.

15. Apparatus for substantially simultaneously applying a plurality of surgical fasteners to body tissue or the like, which comprises a body having a longitudinal portion enclosing axial drive means, a distal portion thereof defining a tissue reception aperture;

fastener closure means positioned at the distal portion of said tissue reception aperture;

fastener holding means pivotally mounted relative to said fastener closure means adjacent one end portion thereof and defining a space therebetween, said fastener holding means containing a plurality of surgical fasteners arranged in generally parallel rows extending generally transversely to said longitudinal portion and fastener pushing means for substantially simultaneously pushing said surgical fasteners;

releasable means for longitudinally advancing said fastener holding means distally to a closed position at least sufficient to contact body tissue positioned within said aperture, and for returning said fastener holding means to a proximal position;

means for reception of user applied force and for translating same to distally directed drive force on said axial drive means generally in alignment with said longitudinal portion;

means for translating said distally directed drive force to said fastener pushing means;

first means for applying a biasing force to said fastener holding means to pivot said fastener holding means into an opened position;

second means for initially resisting the biasing force of said first means until said second means moves to a released condition; and, third means for releasing said second means in response to both application of said drive force along said axial drive means and release of said releasable means for longitudinally advancing said fastener holding means.

16. The apparatus of claim 15 wherein said first means comprises a wire spring associated with the body of the apparatus, said wire spring having a proximal portion which is fixed to the fastener body, and a movable distal portion which contacts a boss projecting laterally from the fastener holding means, said wire spring exerting a biasing force on said boss.

17. The apparatus of claim 15 wherein said second means comprises a leaf member associated with the body of the apparatus and having a distal portion for contacting the fastener holding means, said leaf member permitting longitudinal motion of the fastener holding means while preventing pivoting thereof.

18. The apparatus of claim 17 wherein said leaf member comprises a leaf spring with a distal portion in contact with the base of said fastener holding means, said leaf spring applying a biasing force of such magnitude and direction so as to resist the biasing force of said first means.

19. The apparatus of claim 15 wherein said third means comprises an elongated member which is slidably movable from an initial distal position wherein said elongated member prevents said second means from moving to said released condition, to a proximal position wherein said second means is released and free to move to its released condition.

20. The apparatus of claim 19 wherein said elongated member comprises a flexible strip having a longitudinally extending slot.

21. The apparatus of claim 20 wherein said flexible strip is fabricated from a polymeric material.

22. The apparatus of claim 20 wherein the axial drive means comprises a thrust bar having a depending member for engaging said slot of the flexible strip, said thrust bar being longitudinally movable from an initial proximal position wherein said depending member is not in engagement with said slot, to a distal position wherein said depending member engages said slot, and said thrust bar being returnable to a final proximal position wherein said depending member moves said flexible strip to its proximal position for releasing said second means.

23. The apparatus of claim 22 wherein said depending member of the thrust bar has a camming surface for contacting the proximal edge of the flexible strip.

24. The apparatus of claim 15 wherein said axial drive means is offset from the axial centerline of movement of the fastener pushing means.

* * * * *